(12) United States Patent
Welker

(10) Patent No.: US 6,422,737 B1
(45) Date of Patent: Jul. 23, 2002

(54) LIQUID SAMPLE CYLINDER WITH INTEGRAL MIXING PUMP

(75) Inventor: Brian H. Welker, Sugar Land, TX (US)

(73) Assignee: Welker Engineering Company, Sugar Land, TX (US)

( * ) Notice: Subject to any disclaimer, the term of this patent is extended or adjusted under 35 U.S.C. 154(b) by 0 days.

(21) Appl. No.: 09/815,783

(22) Filed: Mar. 23, 2001

(51) Int. Cl.[7] .............................. B01F 5/14; B01F 15/02; B01F 13/06
(52) U.S. Cl. ........................................ 366/272; 366/137
(58) Field of Search ................................ 366/136, 137, 366/131, 272, 97

(56) References Cited

U.S. PATENT DOCUMENTS

| | | | |
|---|---|---|---|
| 1,781,435 A | * | 11/1930 | Carper ........................ 366/137 |
| 1,870,192 A | * | 8/1932 | Butler |
| 2,193,285 A | * | 3/1940 | Kosik ......................... 366/136 |
| 2,362,922 A | * | 11/1944 | Palm |
| 2,474,254 A | | 6/1949 | Kauffman |
| 2,915,023 A | * | 12/1959 | Rapaport ..................... 366/136 |
| 2,995,774 A | | 8/1961 | Pasqauetti |
| 3,142,476 A | * | 7/1964 | Goodwin ..................... 366/272 |
| 3,152,792 A | * | 10/1964 | Goodwin ..................... 366/272 |
| 3,266,430 A | * | 8/1966 | Mylo |
| 3,606,095 A | * | 9/1971 | Kronseder |
| 4,093,407 A | | 6/1978 | Miles |
| 4,193,745 A | * | 3/1980 | Hamilton et al. ............ 366/272 |
| 4,253,808 A | | 3/1981 | White |
| 5,005,982 A | | 4/1991 | Kistner |
| 5,092,751 A | | 3/1992 | Viktora |
| 5,137,368 A | * | 8/1992 | Kristner ...................... 366/272 |
| 5,190,450 A | | 3/1993 | Ghosh et al. |
| 5,447,369 A | * | 9/1995 | Boxall ........................ 366/136 |

FOREIGN PATENT DOCUMENTS

| | | |
|---|---|---|
| DE | 27 47 972 A 1 | 5/1979 |
| DE | 478353 | 6/1979 |
| WO | WO 84/01004 | 3/1984 |

OTHER PUBLICATIONS

Welker Crude Oil Sample, no date.
Welker Engineering Company Crude Oil Sample Container, J–33 (10/80).

* cited by examiner

Primary Examiner—Tony G. Soohoo
(74) Attorney, Agent, or Firm—Blackwell Sanders Peper Martin LLP

(57) ABSTRACT

An apparatus for mixing dissimilar fluids or fluids having different densities is disclosed. A piston shaped for a close fit and slidably mounted within a tubular member divides a material container into a pressurized end and a mixing chamber. A pump is sealably attached to a base plate. The pump communicates with the mixing chamber through an inlet. The outlet bore is directed so that the discharging mixture from the pump causes a turbulent mixing action within the mixing chamber.

13 Claims, 4 Drawing Sheets

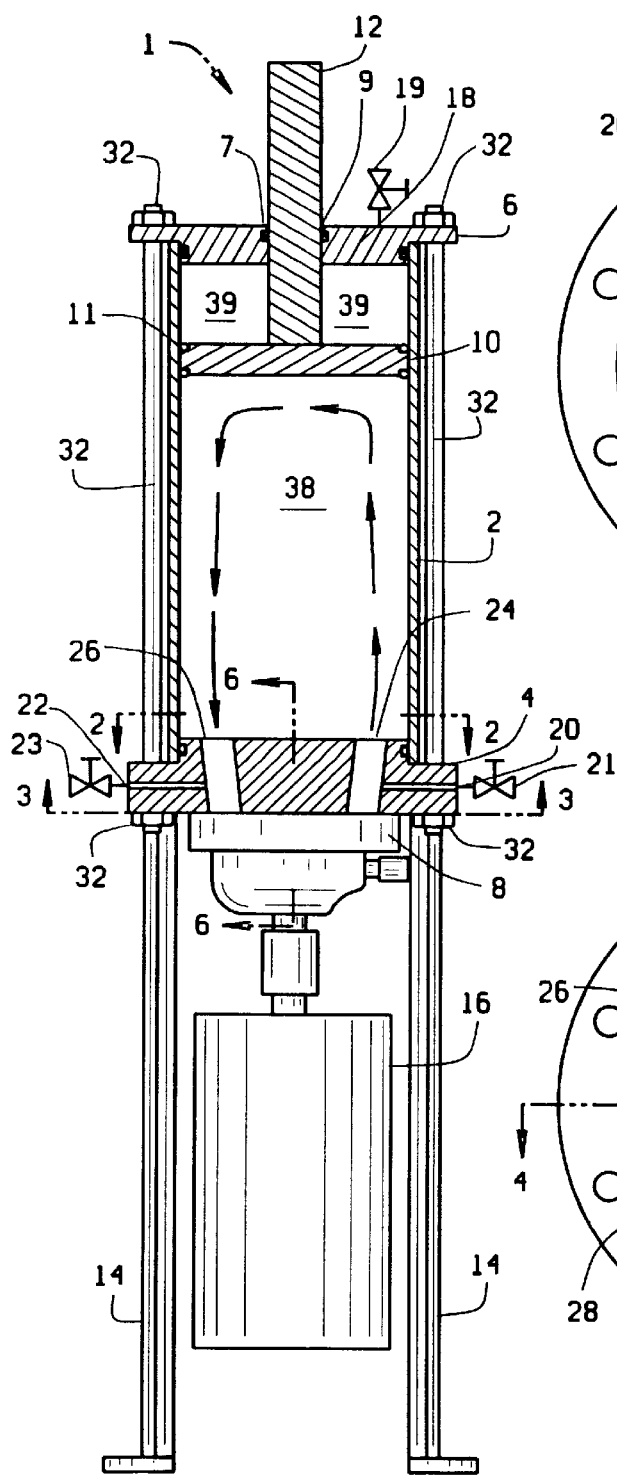
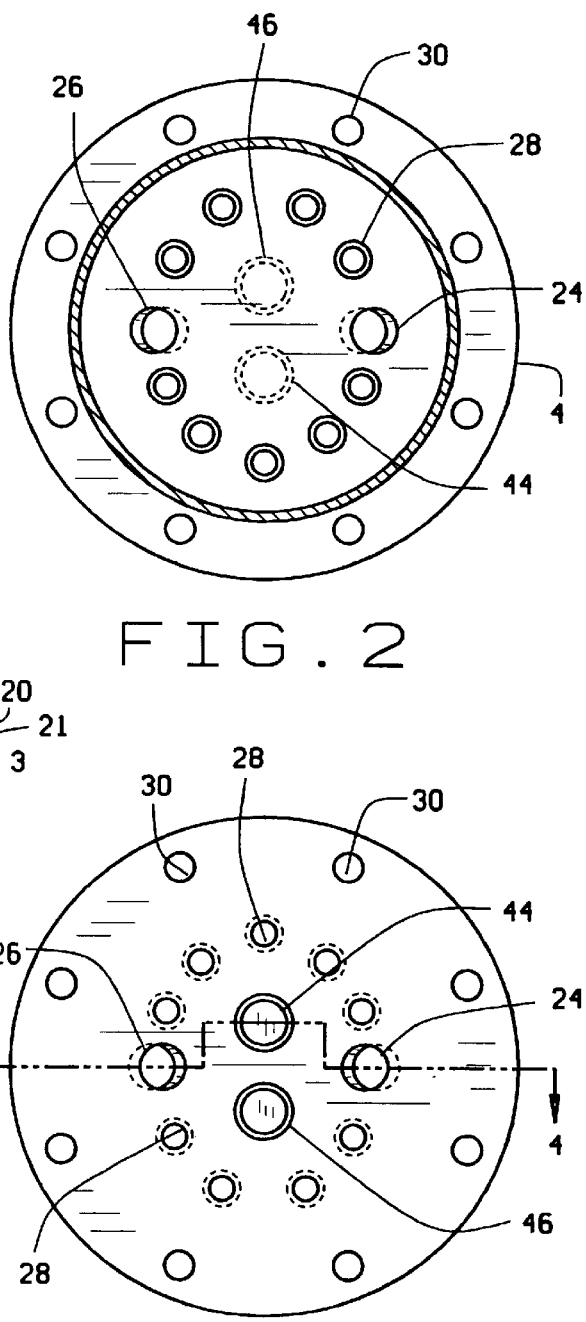
FIG. 1
FIG. 2
FIG. 3

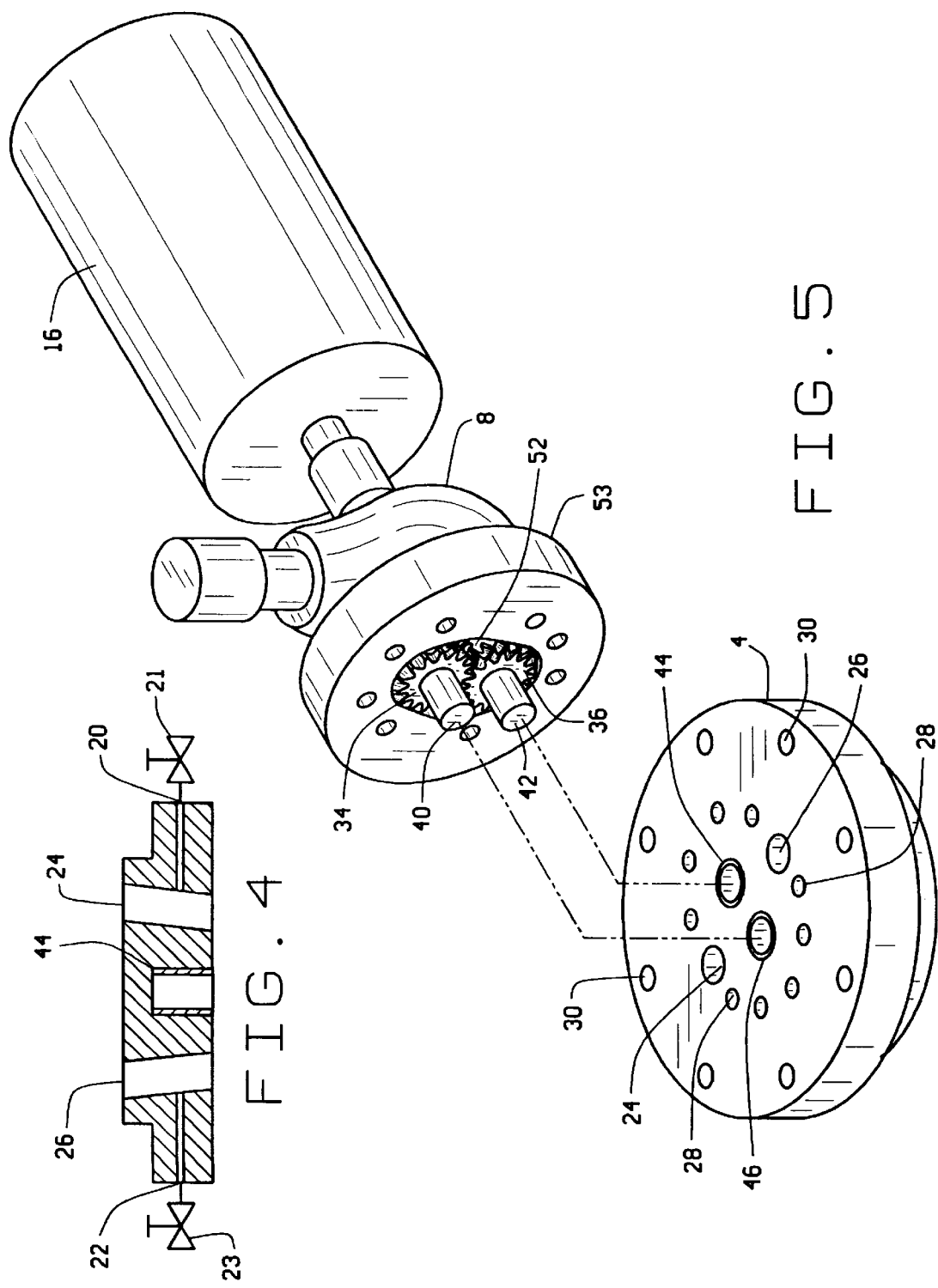

LIQUID SAMPLE CYLINDER WITH INTEGRAL MIXING PUMP

BACKGROUND OF THE INVENTION

1. Field of the Invention

The present invention relates generally to a mixing apparatus. More particularly, the present invention relates to a mixing apparatus without extensive external piping to reduce the risk of cross-contamination from one sample to the next.

2. Brief Description of Prior Art

Mixing apparatus have been developed for a variety of special applications to improve the rheological properties of the components being mixed.

Welker Engineering Company, the assignee of the present patent application, has previously produced a prior art crude oil sampler system which includes a crude oil sample container and mixer. Drawings of this prior art apparatus are included in the Information Disclosure Statement filed concurrently with this patent application. As sample accumulates in this prior art sample container, which is at atmospheric pressure, it stratifies according to the specific gravity of the various fluids in the sample. These fluids need to be mixed into a homogeneous composition before a small amount of sample is drawn from the container for laboratory analysis at a location that is typically remote from the crude oil sample container.

In order to circulate the fluids in the prior art crude oil sample container, a mixer is attached to the container. The mixer includes a motor, a pump, and external piping running from the base of the container to the pump and back to the container.

The sample containers in the prior art Welker crude oil sampler system range in size from 2–30 gallons. In the smaller sizes, the external piping is ½". Larger size containers use larger piping. The volume of fluid in the external piping and the pump varies depending on the size of pipe, but it is a quart of fluid or more.

The external piping runs from the bottom of the container and connects to the suction side of the pump. Additional external piping runs from the discharge side of the pump to the container. On the inside of the container and connected to the external piping is the mixing pump return. (Also sometimes called a down comer).

The down comer is an elongate piece of pipe with a plurality of holes in the sides to spray the fluid back into the sample container. The down comer has a plug in the end, which also has several holes so fluid can sweep the bottom of the container.

Before a sample is drawn for laboratory analysis, the prior art mixer is turned on to circulate the fluids in the sample container. As the fluids are circulated they become more homogenous. The International Standards Organization (ISO-3171) recommends that crude oil be circulated at a rate of one volume of the sample container per minute before a sample is drawn.

The gravity of fluids placed in the sample container may vary from API°8 to 45. Depending on the gravity of the crude oil, and ambient conditions, a heat blanket may first be placed on the sample container before circulation is attempted. Circulation of the fluids in the sample container may last for up to 45 minutes depending on the circumstances, but a typical mixing time is about 15 minutes.

After the fluids have been circulated and the sample has been drawn it is time to clean up. To clean the prior art sample container and purge the external piping and pump, the crude oil is first pumped out. An inert fluid, such as kerosene, is then pumped into the sample container and circulated. The dirty inert fluid is then pumped out. Clean inert fluid is then pumped into the sample container and circulated. The dirty inert fluid is then pumped out. The container is opened and wiped out and the external piping is drained. After the container is closed, it is ready for the next sample. The amount of time it takes to clean the system varies, depending on the size, but a typical clean up time is about 20 minutes. Sometimes operators cut corners and this purging process does not completely clean out the external piping or pump, which can lead to cross-contamination. There is a need to reduce or eliminate the external piping to and from the pump to reduce the chance of cross-contamination.

In an alternative embodiment of the prior art crude oil sample container, a spray nozzle is located in the sample container instead of the down comer. This alternative embodiment likewise had external piping connecting the sample container and the pump. Because of the external piping, this alternative embodiment also has the potential problem of cross-contamination.

Another prior art apparatus produced by Welker is the constant pressure crude container. This apparatus contains several gallons of liquid and also includes a mixer. Drawings of this prior art apparatus are also included in the Information Disclosure Statement filed concurrently with this patent application. A sliding piston divides the constant pressure crude container into a pressurized precharge end and a sample end.

Pressurized gas in the precharge end is utilized to maintain a pressure on the sliding piston. The piston transfers pressure to the sample components to prevent vaporization loss. Sample components are drawn from the sample end of the container through external pipes to the pump, where they are forced through external pipes back to the container and are sprayed through small orifices resembling a showerhead on the sample side of the piston.

The prior art constant pressure crude container, like the crude oil sample container needs to be cleaned and the external piping and the pump must be purged after each use. Failure to properly clean and purge can lead to cross-contamination of the next sample by the prior sample.

The type of pump used in these prior art devices is primarily a matter of manufacturing choice. In the prior art crude oil sampler systems Welker Engineering Company has used a model 2S rotary gear pump with helical gears from Brown & Sharpe of North Kingston, R.I. This pump produces about 9 gpm at 1750 rpm. The model 2S pump from Brown & Sharpe is also used in the 0–200 psi prior art constant pressure crude containers. In prior art constant pressure crude containers with higher pressure ratings a series 5K model 67-L-3461 magnetic drive gear pump from Micropump of Vancouver, Washington is used. The Micropump apparatus is rated at about 5 gpm at 1750 rpm with a 100 psi differential. Regardless of what type of pump is used, the external piping and pump still needs to be purged. There is a need to reduce or eliminate the external piping to and from the pump to reduce the chance of cross-contamination.

U.S. Pat. No. 5,005,982 (Kistner) discloses rotatably mounted intermeshing gears in a chamber between an inlet for introducing components therein and an outlet for discharging components therefrom, wherein the rotating gears shear and extrude the components passing between the gears. Kistner teaches a material processor, using rotating gears having intermeshing teeth, for improving the rheological properties of the components being mixed. The Kistner device is designed to crush and mix the components passing through the rotating gears by providing several different clearances between slowly moving processor teeth. The components being mixed are sheared and extruded as they pass between the teeth before being discharged. The increased clearances between the processor teeth required to crush larger particles, however, limit the Kistner device to rotating the intermeshing gears at speeds that would allow the driven gear to be forced ahead and out of contact with the drive gear by the material therebetween. This typically requires the gears to be rotated at relatively slow speeds. The slow-rotating intermeshing gears provide minimal velocity to materials being discharged from the outlet.

U.S. Pat. No. 2,995,774, issued to Pasquetti, discloses another mixing apparatus. The Pasquetti apparatus is used for thick masses. It utilizes at least two screw-like intermeshed blades mounted on parallel shafts, for effecting an overall movement of material parallel to the screw-like blades. The material is thus alternately placed under high pressures and then forced into thin layers which move along the screw-like blade before being discharged.

Although the apparatus of Kistner and Pasquetti and the two prior art Welker devices achieved some degree of circulation of the fluid, a better mixer is still needed. In addition, mixing devices utilizing remote pumps and piping must be drained and flushed after each use in order to avoid cross-contamination by residual components within the pipes.

A need exists for an apparatus that eliminates external piping from a container to a pump. Such an apparatus would be particularly useful to avoid cross-contamination of batch samples such as those taken in the oil industry. There is also a need in some circumstances for a faster mixer.

SUMMARY OF INVENTION

In the oil industry batch sampling is common. Periodically small samples (for example 20 cc. each) of fluids are put into a holding container. These liquids tend to stratify over time. Before taking a sample back to the laboratory for analysis, it is best to mix fluids to achieve a homogenous sample. As each small sample is hoped to be representative of a large volume of fluid, homogenization and minimization of contamination are significant concerns. The present invention does not require external piping to transfer components to the mixing pump and back to the container. Because there is no external piping to the pump, the present invention minimizes the possibility of cross-contamination. The present invention directs the fluid entering the pump intake and exiting the pump outlet so that a mixing turbulence is created within the material container, in addition to the mixing action of the intermeshing gears within the pump. The present invention appears to mix stratified fluids more quickly and more thoroughly then prior art devices. Clean up of the present invention will also be shorter.

BRIEF DESCRIPTION OF THE DRAWINGS

FIG. 1 is an elevation view with a partial longitudinal section view showing the liquid sample cylinder with integral mixing pump.

FIG. 2 is a section view taken along lines 2—2 of FIG. 1 showing the top face of the base plate.

FIG. 3 is a section view taken along lines 3—3 of FIG. 1 showing the bottom face of the base plate.

FIG. 4 is a section view of the base plate taken along lines 4—4 of FIG. 3 showing the directional angle of the pump intake bore and pump outlet bore, as well as the pump gear shaft bearing bore.

FIG. 5 is an exploded isometric view showing the relationship between the pump and the base plate.

DESCRIPTION OF THE PREFERRED EMBODIMENT

Figure 6:
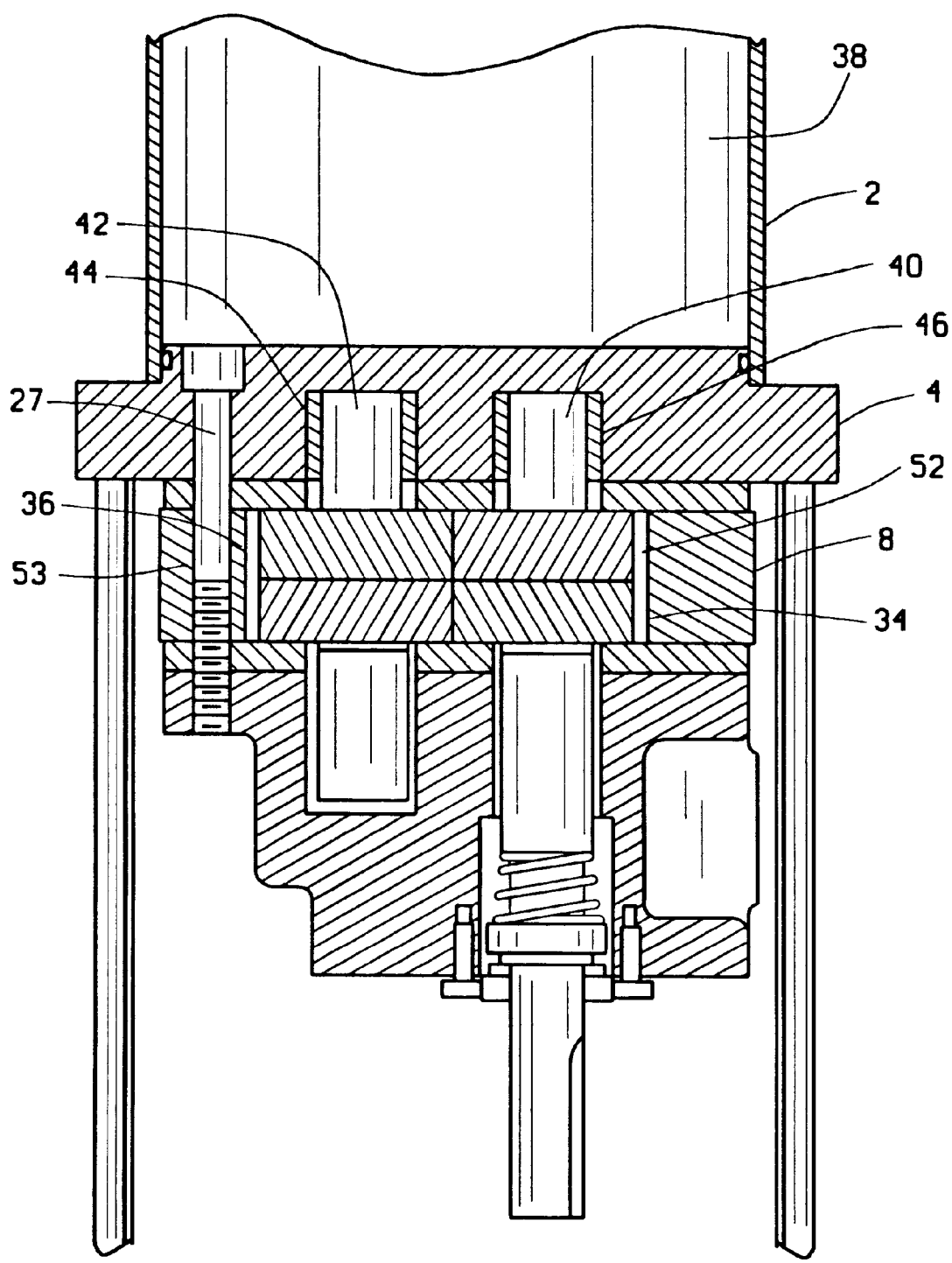
FIG. 6 is a partial transverse section view along lines 6—6 of FIG. 1 showing the assembled base plate and pump in the preferred embodiment.

For the purposes of promoting an understanding of the principles of the invention, reference will now be made to the embodiment illustrated in the drawings and specific language will be used to describe the same. It will nevertheless be understood that no limitation of the scope of the present invention is thereby intended, such alterations and further modifications in the illustrated device, and such further application of the principles of the invention as illustrated therein being contemplated as would normally occur to one skilled in the art to which the invention relates.

FIG. 1 shows the major components of the liquid sample cylinder with integral mixing pump which is generally identified by the numeral 1. The tubular member 2 is generally but not necessarily round in shape, having an internal bore that is generally round in shape for closely receiving a slidable piston 10. Tie bolts 32 hold tubular member 2 between end cap 6 and base plate 4. Seal 3 creates a seal between base plate 4 and tubular member 2. Seal 5 creates a seal between end cap 6 and tubular member 2. End cap 6, has a port 18 connected to a shut off valve 19. End cap 6 also has a generally round opening 7 and contains at least one resilient seal 9 for receiving indicator rod 12. Port 18 and valve 19 are connected to a source of pressurized gas, not shown, which can be preset to maintain the desired pressure in the pressure chamber. Piston 10 is slidably mounted within the internal bore of tubular member 2. Piston 10, having at least one resilient sealing ring 11 around its circumference, divides tubular member 2 into two chambers, pressure chamber 39 and mixing chamber 38. Indicator rod 12, shaped for closely sliding through central opening 7 in end cap 6, is attached to piston 10 to indicate the fill level of mixing chamber 38. Base plate 4, has two ports 20 and 22, connected respectively to valves 21 and 23. Port 20 is connected to the source of the small sample components which are periodically pumped into mixing chamber 38. Port 22 is used to extract a mixed sample for analysis as well as to unload mixing chamber 38 before a new mixture is processed.

Pump 8 is generally a gear pump with the preferred embodiment having, but not being limited to, herringbone style gears. Applicant has found that a Brown and Sharp model 507 pump with herringbone gears is suitable for this application. Other gear styles commonly known to those skilled in the art, such as helical or straight-cut gears, may also be used. Selection of which is primarily a matter of manufacturing convenience.

Pump 8 is attached to base plate 4 so that pump intake bore 26 communicates with the intake side (also known as the suction side) of pump chamber 52 (also known as the discharge side) better seen in of FIG. 5, as well as mixing chamber 38. Pump exhaust bore 24 communicates with the exhaust side (also known as discharge side) of pump chamber 52 of FIG. 5, as well as mixing chamber 38. Motor 16 is connected to pump 8 to provide operator controlled power to the pump. Electric and pneumatic motors are suitable for this purpose. Specifically, applicant has found a model V6C pneumatic motor from J. H. Fenner & Co., Limited of Rockford, Ill. is suitable for this purpose. When powered by this Fenner pneumatic motor, the Brown and Sharp Model 507 pump described above is rated to operate at 1725 rpm with a displacement of approximately 3 gallons per minute. The size of the intake bore 26 and exhaust bore 24 will vary with the size of the mixing chamber 38. For a three gallon mixing chamber 38, bore 26 and bore 24 have a diameter of approximately ¾ inch and will hold about 12 cc. of fluid. A plurality of legs 14 are attached to base plate 4 to hold the apparatus in an upright position shown in phantom are bearing pockets 44 and 46.

FIG. 2 depicts the top view of base plate 4, showing the plurality of holes 28 used to receive bolts, not shown, to attach pump 8. The directional angle of pump intake bore 26 and pump exhaust bore 24 is shown in phantom. Also shown in the top view of the base plate 4 is the circular array of tie bolt holes 30.

FIG. 3 depicts the bottom view of base plate 4. This view shows the two bearing pockets 44 and 46 for supporting parallel gear shafts 40 and 42. Intake bore 26 and exhaust bore 24 are positioned near the center of plate 4. The tie bolt holes 30 are arranged in circular fashion around the outer periphery.

FIG. 4 shows a section view of base plate 4, taken along lines 4—4 of FIG. 3, illustrating one of the bearing pockets 44 as well as pump inlet bore 26 and pump outlet bore 24. Also depicted in this view are port 20, used for inputting sample materials to the chamber 38, and port 22 used for unloading samples.

FIG. 5 depicts an exploded view of base plate 4 and pump 8 illustrating pump chamber 52, which is defined by base plate 4 and pump housing 53. Pump chamber 52 contains parallel gear shafts 40 and 42 as well as intermeshing drive gear 34 and intermeshing driven gear 36. The pump 8 is driven by the motor 16. Fluid enters the chamber 52 through the pump inlet bore 26 and is transferred to the opposite side of the chamber 52 by action of the gears 34 and 36. The fluid then exits the chamber 52 through the pump exhaust bore 24.

FIG. 6 depicts a partial section view taken along lines 6—6 of FIG. 1 illustrating the assembled pump chamber 52. A bolt 27 fits through one of the holes 28 in base plate 4 and threadedly engages pump housing 53. A plurality of other bolts, not shown, fit in each hole 28 to securely connect the pump 8 to the plate 4. The pump 8 is assembled to base plate 4 with drive gear 34 and driven gear 36 on parallel gear shafts 40 and 42, within bearing pockets 44 and 46 respectively. A pump chamber 52 surrounds the gears 34 and 36.

Figure 7:
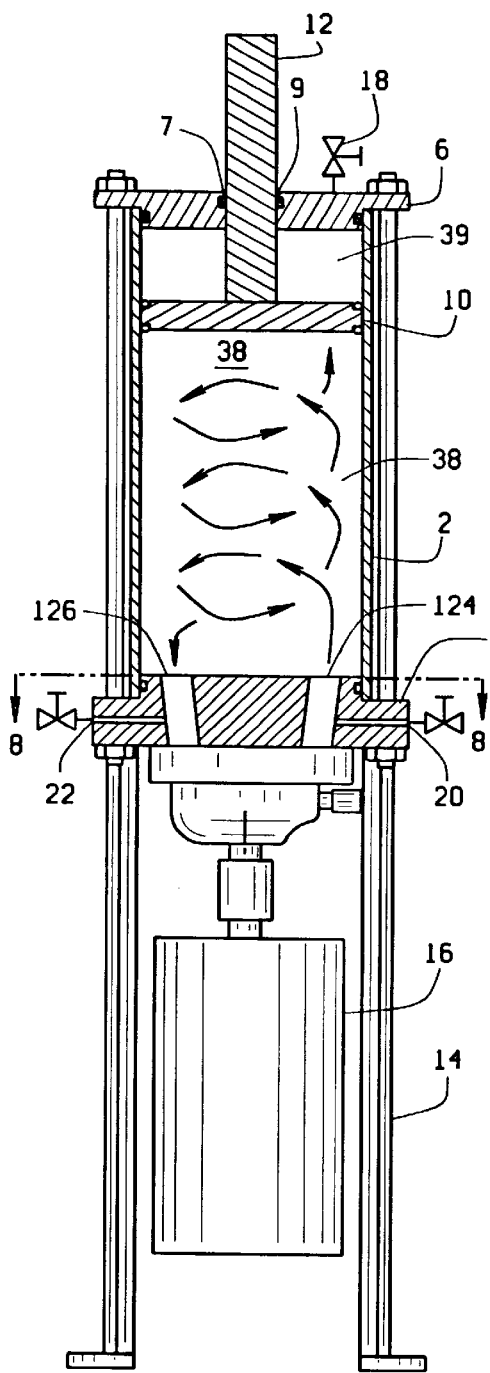
FIG. 7 is an elevation view with a partial longitudinal section view showing an alternative embodiment of the liquid sample cylinder with integral mixing pump.

FIG. 7 depicts an alternative embodiment of the present invention wherein pump inlet bore 126 and pump exhaust bore 124, located in base plate 104, are directed at compound angles to convey a rotary mixing turbulence in mixing chamber 38. All other components are the same.

Figure 8:
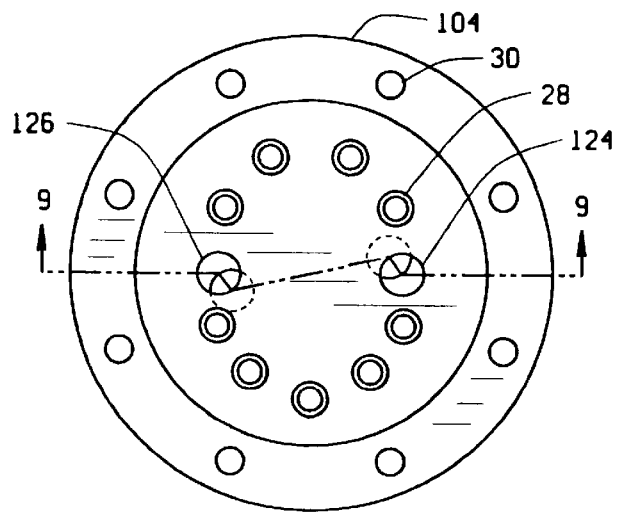
FIG. 8 is a section view taken along lines 8—8 of FIG. 7 showing the top face of the base plate in the alternative embodiment.

FIG. 8 depicts the top view of base plate 104 in the alternative embodiment, showing the plurality of holes 28 used to attach pump 8, as well as the compound angle of pump intake bore 126 and pump exhaust bore 124. Also shown in the top view of base plate 104 is a circular array of tie bolt holes 30.

Figure 9:
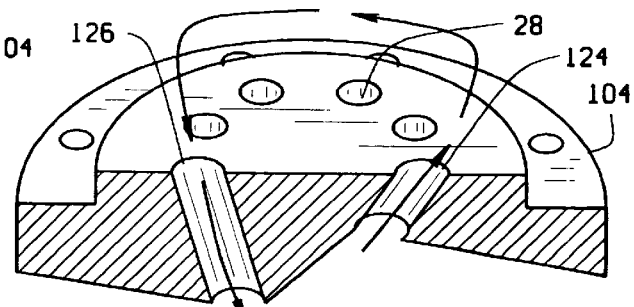
FIG. 9 is a sectioned isometric view of the base plate along lines 9—9 of FIG. 8 showing the compound angle of the pump intake bore and pump outlet bore in the alternative embodiment.

FIG. 9 depicts a section view of base plate 104, taken along lines 9—9 of FIG. 8, illustrating the directional orientation of the compound angles of pump inlet bore 126 and pump exhaust bore 124.

Figure 10:
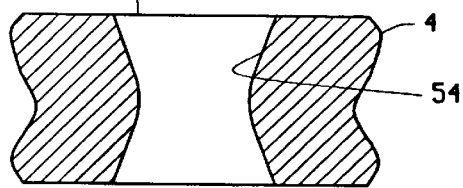
FIG. 10 is a partial section view of the base plate for a third alternative to the preferred embodiment showing a venturi within the pump outlet bore.

FIG. 10 shows a partial section view of base plate 4, along lines 4—4 of FIG. 3, illustrating a modification of the preferred embodiment of the present invention wherein pump exhaust bore 24 contains a venturi 54 to cause a pressure differential of mixed components exiting pump chamber 52 and entering mixing chamber 38 to further increase the turbulence-causing force conveyed to components within mixing chamber 38.

Figure 11:
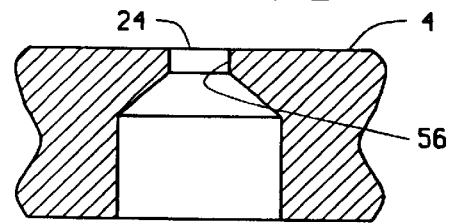
FIG. 11 is a partial section view of the base plate for a fourth alternative to the preferred embodiment showing a nozzle within the pump outlet bore.

FIG. 11 shows a partial section view of base plate 4, along lines 4—4 of FIG. 3, illustrating a third modification of the present invention wherein pump exhaust bore 24 contains nozzle 56 to increase the velocity of mixed components exiting pump chamber 52 and entering mixing chamber 38, to further increase turbulance-causing force conveyed to the components within mixing chamber 38.

What is claimed is:

1. An apparatus for mixing dissimilar fluids, or fluids having different densities, comprising:
    (a) a material container defined by a tubular member having a bore shaped for closely receiving a piston, said material container having a pressure end, the pressure end having an end cap sealably attached, and a mixture end having a base plate sealably attached, the end cap having a port adapted for connecting a conduit for supplying pressurized gas to the port, the base plate having a first port adapted for connecting a conduit for supplying sample components to said to material container and a second port adapted for connecting a conduit for unloading mixed sample components from said material container, and also having an inlet bore and an outlet bore for communicating sample fluids between said material container and a pump,
    (b) a piston shaped for a close fit and slidably mounted within said tubular member so that the piston divides the material container into a pressure end and a mixing end, said piston assembly having at least one resilient sealing ring,
    (c) a pump sealably attached to the base plate, said pump communicating with the mixing chamber through an inlet bore originating in the mixing chamber and terminating at said pump, for introducing sample components therein, and an outlet bore originating at said pump and terminating in the mixing chamber for discharging mixtures therefrom, the inlet bore and the outlet bore being directed so that the discharging mixture causes a turbulent mixing action within the mixing chamber,
    (d) a source of compressed gas suitably connected to the first port in the end cap by a suitably sized conduit,
    (e) a source of power suitably connected to the pump.

2. A mixing apparatus as recited in claim 1, wherein the inlet bore and the outlet bore in the base plate are directed at divergent angles so that a mixture entering the mixing chamber causes a rolling turbulence within said mixing chamber.

3. A mixing apparatus as recited in claim 2, wherein the pump further comprises:
   (a) a pump chamber, said pump chamber defined by a pump housing and a base plate, said pump chamber having at least two rotatably mounted intermeshing gears therein.

4. A mixing apparatus as recited in claim 1, wherein the inlet bore and the outlet bore in the base plate are directed at compound angles so that a mixture entering the mixing chamber causes a revolving turbulence within said mixing chamber.

5. A mixing apparatus as recited in claim 4, wherein the pump further comprises:
   (a) a pump chamber, said pump chamber defined by a pump housing and a base plate, said pump chamber having at least two rotatably mounted intermeshing gears therein.

6. A mixing apparatus as recited in claim 1, wherein the outlet bore in the base plate further comprises:
   (a) a venturi therein, allowing a pressure differential of sample fluid exiting the pump through the outlet bore to the mixing chamber, increasing the turbulence of the sample mixture therein.

7. A mixing apparatus as recited in claim 1, wherein the outlet bore in the base plate further comprises:
   (a) a nozzle therein, allowing increased velocity of sample fluid exhausting from the pump through said outlet bore to the mixing chamber, increasing the turbulence of the sample mixture therein.

8. A mixing apparatus as recited in claim 1, wherein the pump further comprises:
   (a) a pump chamber, said pump chamber defined by a pump housing and a base plate, said pump chamber having at least two rotatably mounted intermeshing gears therein.

9. A mixing apparatus as recited in claim 8, wherein said apparatus further comprises:
   (a) said end cap having a central opening shaped closely for receiving an indicator rod, said central opening having at least one resilient ring.

10. A mixing apparatus as recited in claim 8, wherein said intermeshing gears further comprise:
    (a) a parallel drive gear shaft, said drive gear shaft rotatably mounted in the pump chamber and removably attached to at least one of the intermeshing gears, wherein the intermeshing gears are of the herringbone type,
    (b) a parallel driven gear shaft, said driven gear shaft rotatably mounted in the pump chamber and removably attached to at least one of the intermeshing gears, wherein the intermeshing gears are of the herringbone type.

11. A mixing apparatus as recited in claim 8, wherein said intermeshing gears further comprise:
    (a) a parallel drive gear shaft, said drive gear shaft rotatably mounted in the pump chamber and removably attached to at least one of the intermeshing gears, wherein said intermeshing gears are of the helical type,
    (b) a parallel driven gear shaft, said driven gear shaft rotatably mounted in the pump chamber and removably attached to at least one of the intermeshing gears, wherein said intermeshing gears are of the helical type.

12. A method of causing a turbulent mixing action within a material container of a mixing apparatus to reduce stratification of mixed, dissimilar fluids or fluids having different densities, between recycles through a gear pump comprising:
    (a) introducing dissimilar sample fluids to a pressurized mixing chamber,
    (b) transferring said sample fluids through an inlet bore originating in the mixing chamber terminating at a gear pump,
    (c) passing said fluids between rotating intermeshing gears within the pump,
    (d) exhausting said fluid through an outlet bore originating at the pump and terminating in the mixing chamber,
    (e) directing the exhausting mixture to cause a turbulent mixing action within the mixing chamber.

13. An apparatus for mixing dissimilar fluids or fluids having different densities comprising:
    (a) a material container for holding various sample fluid mixtures,
    (b) a piston slidably mounted within the material container such that a desired pressure is maintained within the material container,
    (c) a pump in fluid communication with the material container such that a turbulent mixing action is caused within the material container.

* * * * *